United States Patent
Yao et al.

(10) Patent No.: US 9,636,042 B2
(45) Date of Patent: May 2, 2017

(54) METHODS AND APPARATUSES FOR DETECTING RESPIRATORY RATE

(71) Applicant: Shenzhen Mindray Bio-Medical Electronics Co., Ltd., Shenzhen (CN)

(72) Inventors: Zuming Yao, Shenzhen (CN); Lihan Liu, Shenzhen (CN); Yun Deng, Shenzhen (CN); Jilun Ye, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 14/281,764

(22) Filed: May 19, 2014

(65) Prior Publication Data

US 2014/0257125 A1    Sep. 11, 2014

Related U.S. Application Data

(63) Continuation-in-part of application No. 11/607,605, filed on Dec. 1, 2006, now abandoned.

(30) Foreign Application Priority Data

Aug. 28, 2006  (CN) .......................... 2006 1 0062356

(51) Int. Cl.
*A61B 5/08*         (2006.01)
(52) U.S. Cl.
CPC ................................ *A61B 5/0816* (2013.01)

(58) Field of Classification Search
CPC .................................................... A61B 5/0816
See application file for complete search history.

(56) References Cited

U.S. PATENT DOCUMENTS

2008/0082003 A1    4/2008  Deng et al.

FOREIGN PATENT DOCUMENTS

| CN | 1186646 A | 7/1998 |
|---|---|---|
| CN | 1382417 A | 12/2002 |
| CN | 1736324 A | 2/2006 |

OTHER PUBLICATIONS

Office Action mailed Jan. 17, 2012 for U.S. Appl. No. 11/607,605, filed Dec. 1, 2006.
Office Action mailed Dec. 20, 2013 for U.S. Appl. No. 11/607,605, filed Dec. 1, 2006.

*Primary Examiner* — Christian Jang
(74) *Attorney, Agent, or Firm* — Kory D. Christensen; Stoel Rives LLP

(57) ABSTRACT

This disclosure relates to methods and apparatus for detecting respiratory rate. The method for detecting respiratory rate may include: sampling respiratory waveform data in a time sequence; detecting respiratory cycles from the sampled respiratory waveform data; calculating variation degree for the sampled respiratory waveform data; calculating base length base on the variation degree; calculating smoothed length base on the base length; calculating real-time degree for each respiratory cycle base on the variation degree, sequence number of each respiratory cycle, and the smoothed length; and calculating respiratory rate base on the smoothed length and the real-time degree.

19 Claims, 5 Drawing Sheets

METHODS AND APPARATUSES FOR DETECTING RESPIRATORY RATE

TECHNICAL FIELD

This disclosure relates generally to respiratory monitoring systems. Particularly, this disclosure relates to methods and apparatuses for detecting respiratory rate in respiratory monitoring systems.

BACKGROUND

Respiratory rate is a common physiological parameter in physiological parameters monitoring that is usually measured via impedance pneumography. Respiratory rate is generally calculated by following steps: detecting peaks and valleys from received waveform, calculating duration of each respiratory cycle and stacking the durations into an FIFO (First In, First Out) array, then averaging a number of durations of recent respiratory cycles, where the number is restricted by an accumulated time threshold.

The respiratory rate of a patient may change frequently, because the patient's respiratory impedance can be sensitive to some external factors, such as movement, heart beat and the like. When the respiratory rate of the patient changes from low to high (or from high to low) very quickly and then enters into a relatively stable respiratory state, it is generally desirable that the respiratory rate detected by a patient monitor could reflect the changing respiration trend in a timely manner. But conventional respiratory rate smoothing calculation method may not meet such requirements satisfactorily, and specific problems can be as follows.

1. The respiratory rate is calculated by averaging real-time respiratory rates of several respiratory cycles without considering real-time change in the respiratory rate, so the result may not reflect real-time condition; and 2. In conventional methods, the respiratory rate is calculated using real-time respiratory rates of the latest 12 respiratory cycles without fully considering the influence of respiratory cycles used, which may cause poor smoothness in the result, for example, sudden change can occur in current respiratory rate when real-time respiratory waveform is interfered.

SUMMARY

Disclosed herein are embodiments of methods and apparatuses for detecting respiratory rate.

In one aspect, an method for detecting respiratory rate can include:
  sampling respiratory waveform data in a time sequence;
  detecting respiratory cycles from the sampled respiratory waveform data;
  calculating variation degree for the sampled respiratory waveform data;
    calculating base length based on the variation degree;
    calculating smoothed length based on the base length;
    calculating real-time degree for each respiratory cycle based on the variation degree, sequence number of each respiratory cycle, and the smoothed length; and calculating respiratory rate based on the smoothed length and the real-time degree.

In another aspect, an apparatus for detecting respiratory rate can include:
  a sampling module for sampling received respiratory waveform data in a time sequence;
  a respiratory cycle detection module for detecting respiratory cycles from the sampled respiratory waveform data;
  a variation degree calculation module for calculating variation degree for the sampled respiratory waveform data;
  a base length calculation module for calculating base length based on the variation degree;
  a smoothed length calculation module for calculating smoothed length based on the base length;
  a real-time degree calculation module for calculating real-time degree of each respiratory cycle based on the variation degree, sequence number of corresponding respiratory cycle, and the smoothed length; and
  a respiratory rate calculation module for calculating respiratory rate based on the smoothed length and the real-time degree.

DETAILED DESCRIPTION

In the disclosure, the respiratory rate can be calculated by averaging weighted respiratory rates corresponding to respiratory cycles within certain time duration. Typically human respiration changes slowly and sometimes may experience external interference, which can cause poor signal quality and a drastic change in real-time respiratory rate. Therefore, real-time respiratory rate often needs to be smoothed, and the principle may be as follows:

1. Increase stability and reflect real-time degree for respiration with large variations;

2. Increase real-time degree and reflect respiratory rate change within short time duration for respiration with small variations;

3. Employ more respiratory cycles to perform averaging for respiration with high respiratory rate, so as to enhance stability thereof;

4. Employ less respiratory cycles to perform averaging for respiration with low respiratory rate, so as to enhance real-time degree thereof.

The method for detecting respiratory rate can include the following steps: sampling received respiratory waveform; detecting respiratory cycles; calculating variation degree; calculating variation factor; calculating base length; calculating smoothed length; and calculating respiratory rate.

Figure 1:
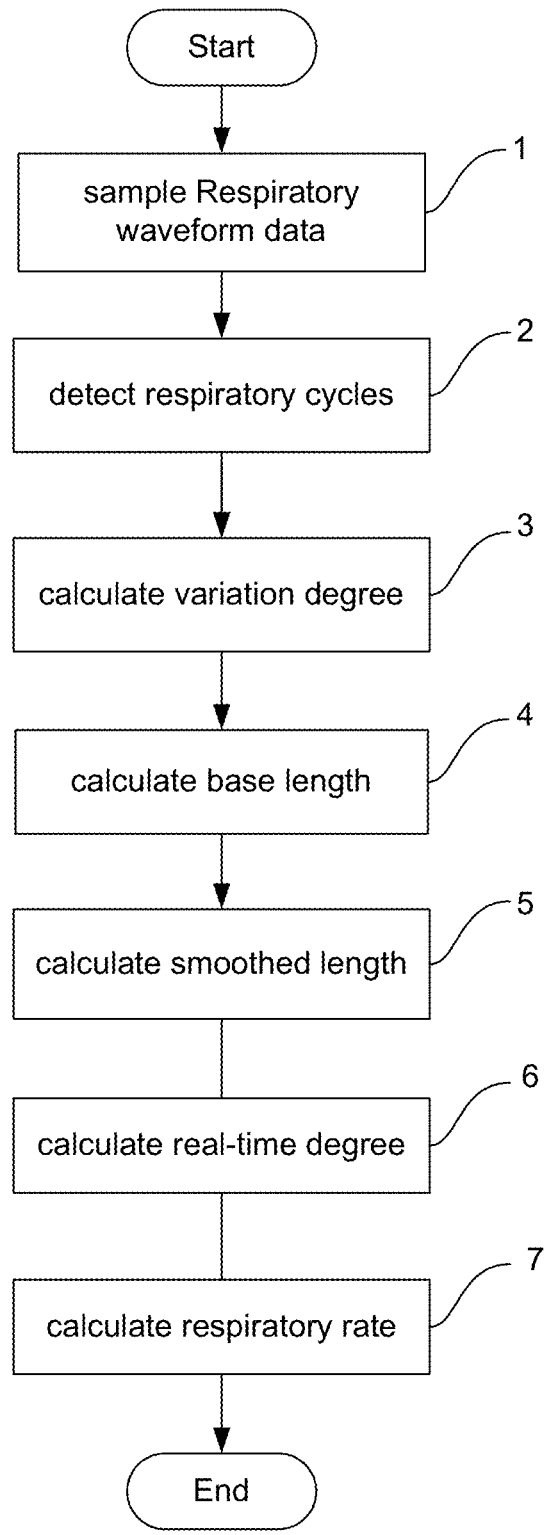
FIG. 1 shows a flow chart of a method for detecting respiratory rate according to an embodiment.

FIG. 1 is a flow chart showing the method for detecting respiratory rate according to an embodiment, which may include the following steps.

At step 1, received respiratory waveform data can be sampled within a time period in a time sequence to obtain a group of samples.

At step 2, respiratory cycles can be detected from the group of samples, which is the sampled respiratory waveform data. Specifically, step 2 may include the following steps:

Firstly, for each respiratory cycle, whether the respiratory cycle is saturated can be evaluated: counting a time duration t in which a series of samples exceed a saturation threshold, if t is greater than a time threshold, for example if t>0.2 s, then the corresponding respiratory cycle is set as saturated state, otherwise the corresponding respiratory cycle is set as unsaturated state.

Secondly, peaks and valleys can be detected from the group of samples: setting a detecting state, when the detecting state is valley searching, if a series of samples decrease continuously, then update valley value in real time, and if the series of samples increase and the increased range (which is value of current sample minus valley value) exceeds a rising threshold, which could be adjusted automatically in every respiratory cycle, then a valley is found and the detecting state is changed to peak searching; when the detecting state is peak searching, if a series of samples increase continuously, then update peak value, and if the series of samples decrease and the decreased range (which is value of current sample minus peak value) exceeds a declining threshold, which could be adjusted automatically in every respiratory cycle, then a peak is found and the detecting state is changed to valley searching. The rising threshold and the declining threshold y can be updated as follows:

$$y = \begin{cases} k*H, x \le \dfrac{T}{2} \\ \left(k - \dfrac{1}{4}\right)*H - \dfrac{H}{2T}*x, x > \dfrac{T}{2} \end{cases},$$

where k is an empirical coefficient that can be within [½, 1], T is the duration of the previous respiratory cycle, H is the peak-to-valley height of the previous respiratory cycle, and x represents the sampling time of a sample corresponding to a respiratory cycle.

Finally, the duration of the respiratory cycle can be obtained from the peaks or valleys detected: the time difference between two adjacent peaks or valleys is the duration of the respiratory cycle.

In addition, in order to improve smoothness further, after the duration of the respiratory cycle is calculated, step 2 can further include:

If the duration difference between the current and previous respiratory cycles is equal to or greater than a difference threshold and the current respiratory cycles is saturated, the duration of the current respiratory cycle can be smoothed by the duration of the previous respiratory cycle. Specifically, this can be realized as follows:

The duration of each respiratory cycle can respectively be recorded with two respiratory cycle arrays in chronological order. The first array can record the detected respiratory durations, while the second array can record the affirmed respiratory durations.

When the current respiratory cycle is saturated: if the difference between the durations of the current and previous respiratory cycles recorded in the first array is equal to or greater than a difference threshold, then the duration of the previous respiratory cycle is used as the duration of the current respiratory cycle, which is then recorded in the second array; if the difference between the durations of the current and previous respiratory cycles recorded in the first array is less than the difference threshold, then the duration of the current respiratory cycle is recorded in the second array, and the saturation status can then be cleared. For all other situations, the duration of the current respiratory cycle can be recorded in the second array. The difference threshold can be chosen as 20%.

At step 3, variation coefficient and variation degree can be calculated.

Firstly, a set of variation coefficients can be calculated for the group of samples. The variation coefficient between two adjacent samples cv can be calculated by $$cv = \frac{d1 - d2}{(d1 + d2)/2},$$

where d1 and d2 are two samples, d1≥0, d2≥0 and d1 and d2 cannot be 0 at the same time. For a group of samples s(N) (N is the number of samples), variation coefficient can be calculated for adjacent samples.

The variation coefficient is a relative value, which may reflect the change between two adjacent samples:

If d1=d2, then cv=0, indicating there is no variation between the two adjacent samples;

If d1 or d2 is equal to 0, then cv=2, indicating the largest change between the two adjacent samples;

If d1 is greater than d2, then cv>0, indicating d1 increases with respect to d2 and the value of the variation coefficient cv can reflect the amount of such increase; and If d1 is less than d2, then cv<0, indicating d1 decreases with respect to d2 and the value of the variation coefficient cv can reflect the amount of such decrease.

Secondly, the variation degree for the group of samples is determined. Two critical values are provided: lcv is a smaller critical value and mcv is an intermediate critical value, where 0≤lcv<mcv<2. Numbers lcnt and mcnt of the variation coefficients belonged to [0, lcv] and [0, mcv] is counted respectively.

Then, whether $$\frac{lcnt}{N}$$

is greater than or equal to a first threshold (such as whether $$\frac{lcnt}{N} \ge 80\%\bigg).$$

If yes, the variation degree for the group of samples is considered low; otherwise, whether $$\frac{mcnt}{N}$$

is greater than or equal to the first threshold (such as whether $$\frac{mcnt}{N} \ge 80\%\bigg),$$

if yes, the variation degree for the group of samples is considered intermediate, otherwise the variation degree for the group of samples is considered high. In practical applications, the fist threshold may be adjusted to other values as required.

In the embodiment, a variation factor could be used to reflect the variation degree for the group of samples. When the variation degree for the group of samples is high, the variation factor n is 0; when the variation degree of the group of samples is intermediate, the variation factor n is 1; when the variation degree for the group of samples is low, the variation factor is 2.

At step 4, base length is calculated.

The value of the base length is adopted as the bigger one from a reference cycles number and a minimum empirical period number during a predetermined time. Where the predetermined times corresponding to different variation degrees are different, specifically the predetermined time is a first time period when the variation degree is low, the predetermined time is a second time period when the variation degree is intermediate, the predetermined time is a third time period when the variation degree is high, and the first time period<the second time period<the third time period; the reference cycles number is the number of respiratory cycles calculated base on the previous respiratory rate and the predetermined time period; the minimum empirical period number is a empirical value.

For example, the first time period is 10 s, the second time period is 15 s and the third time period is 20 s. When the variation degree is low and the minimum empirical period number is 5, the base length is MAX (5, 10*the previous respiratory rate/60); when the variation degree is intermediate and the minimum empirical period number is 6, the base length is MAX(6, 15*the previous respiratory rate/60); when the variation degree is high and the minimum empirical period number is 7, the base length is MAX(7, 20*the previous respiratory rate/60).

Figure 3:
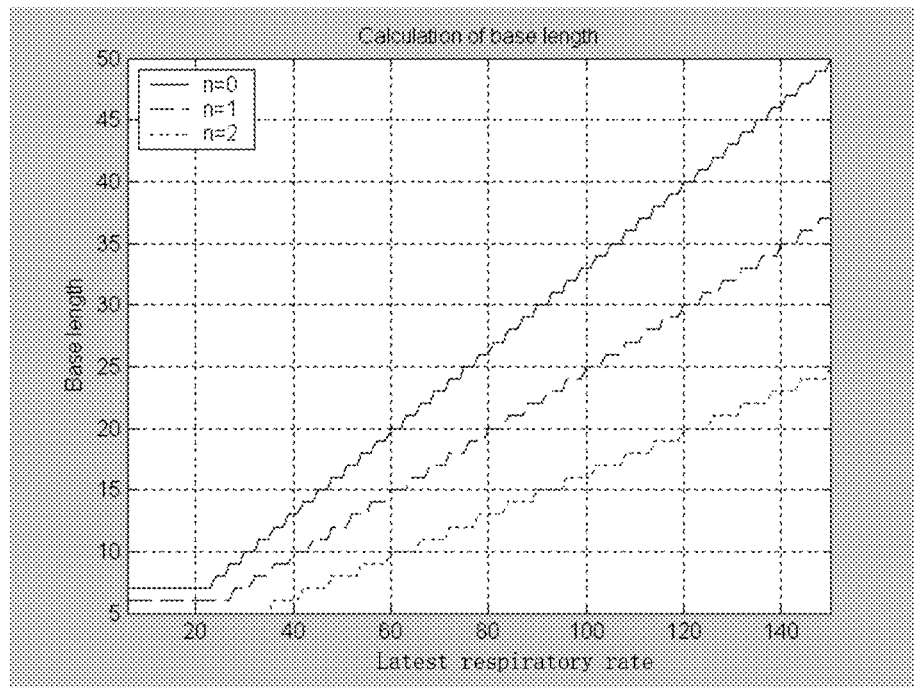
FIG. 3 shows a simulated diagram of relationship between base length and the latest respiratory rate according to the method for detecting respiratory rate shown in FIG. 1.

The relationship between the previous respiratory rate and the base length may be best depicted with a view in MATLAB, for example, as shown in FIG. 3, where n is a variation factor.

From the calculation of the base length, it can be seen that the base length is related to the variation degree for the group of samples. The base length increases with the increase of the latest respiratory rate. And the higher the variation degree is, the faster the base length increases with the increase of the latest respiratory rate.

The predetermined first, second and third time period could not be too long or too short. A longer time period leads to slower change and a larger number of respiratory cycles; a shorter time period leads to a faster change and a smaller number of respiratory cycles.

At step 5, smoothed length is calculated.

It is defined that the relationship between the smoothed length and the base length is given by the following equation:

$$\sum_{i=sl-bl+1}^{sl} i^n \geq th_2 * \sum_{i=1}^{sl} i^n$$

where i is the sequence number indicating the position of the respiratory cycle, n is the variation factor and n≥0, $th_2$ is a second threshold, bl represents the base length, sl represents the smoothed length, and sl is the minimum integer satisfying the equation. The second threshold $th_2$ could be 90% or other values as required.

Figure 4:
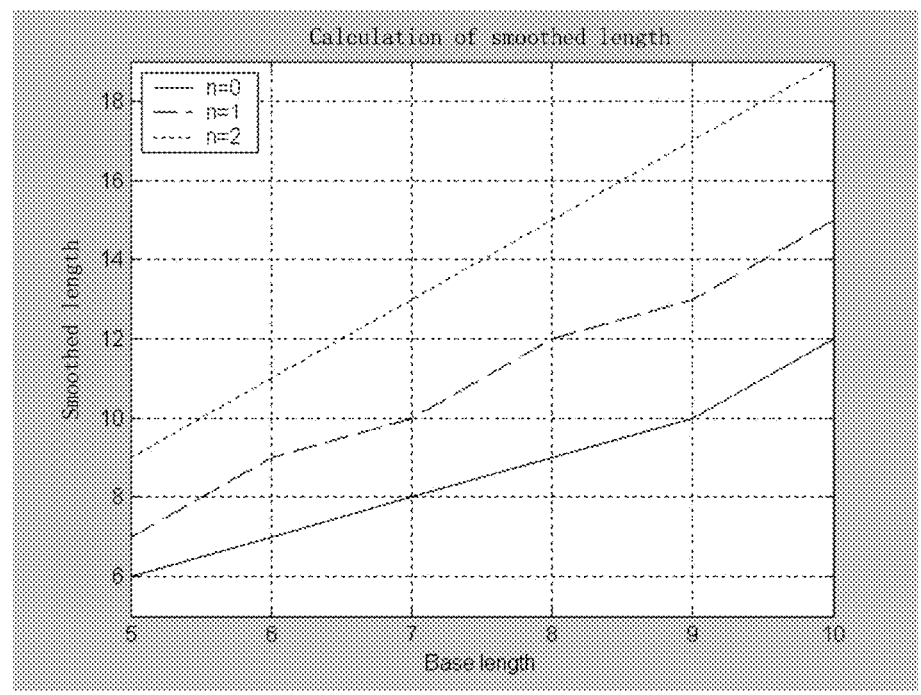
FIG. 4 shows a simulated diagram of relationship between smoothed length and base length according to the method for detecting respiratory rate shown in FIG. 1.

Once the base length is determined, the smoothed length may be calculated. The relationship between the smoothed length and the base length is best depicted with a view in MATLAB, for example, as shown in FIG. 4, where n is the variation factor.

Figure 5:
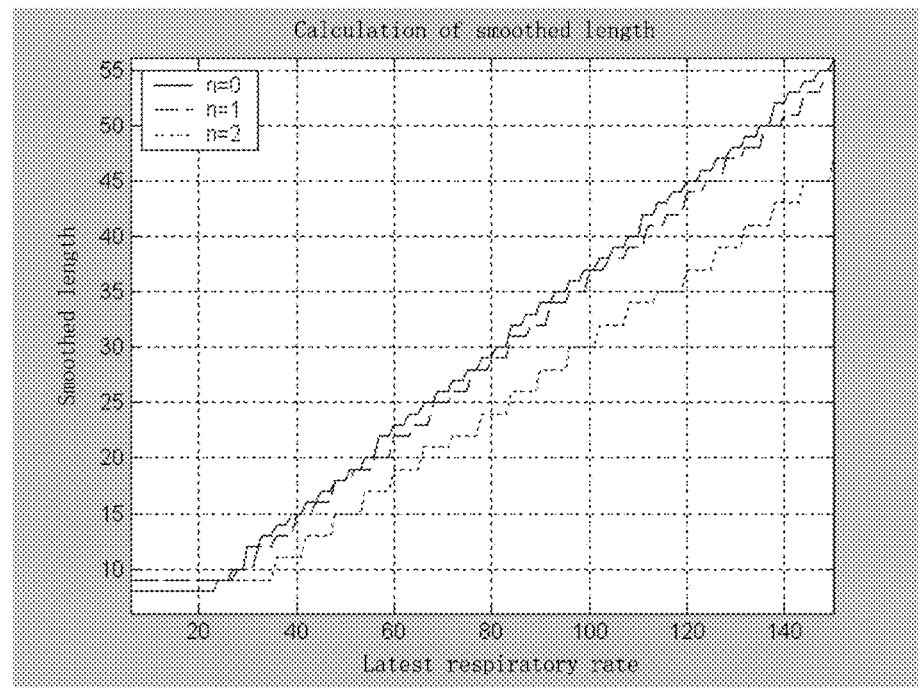
FIG. 5 shows a simulated diagram of relationship between smoothed length and the latest respiratory rate according to the method for detecting respiratory rate shown in FIG. 1.

The relationship between the previous respiratory rate and the smoothed length is best depicted with a view in MATLAB, for example, as shown in FIG. 5, where n is the variation factor.

At step 6, real-time degree and the variation factor are calculated.

Firstly, real-time weight is determined. Each respiratory cycle corresponds to a real-time weight, and the real-time weight and the sequence number of corresponding respiratory cycle is an exponential relationship. That is $p(i)=i^n$, where p(i) is the real-time weight, i is the sequence number of corresponding respiratory cycle, and n is the variation factor.

Then, the real-time degree is calculated. The real-time degree specifies the closeness between sampling time of the respiratory cycle and current time. A higher real-time degree indicates that the respiratory cycle has a better real-time performance. The real-time degree rt(i) can be calculated by $$rt(i) = \frac{i^n}{\sum_{i=1}^{sl} i^n},$$

where i is the sequence number of corresponding respiratory cycle, a sequence number indicating the position for a preceding respiratory cycle is smaller than a sequence number indicating the position for a subsequent respiratory cycle, n is the variation factor, n≥0, and sl is the smoothed length.

Taking the latest 10 respiratory cycles as an example, Table. 1 below lists the relationship between the real-time degree and the variation factor.

TABLE 1

| Sequence number | 1 | 2 | 3 | 4 | 5 | 6 | 7 | 8 | 9 | 10 |
| --- | --- | --- | --- | --- | --- | --- | --- | --- | --- | --- |
| Time direction of sequence number | | | | Past | ---------- | ---------- | ---------- | -----> | Now | |
| Real-time weight (variation factor = 0) | 1 | 1 | 1 | 1 | 1 | 1 | 1 | 1 | 1 | 1 |
| Real-time degree | 0.1 | 0.1 | 0.1 | 0.1 | 0.1 | 0.1 | 0.1 | 0.1 | 0.1 | 0.1 |
| Real-time weight (variation factor = 1) | 1 | 2 | 3 | 4 | 5 | 6 | 7 | 8 | 9 | 10 |

TABLE 1-continued

| Sequence number | 1 | 2 | 3 | 4 | 5 | 6 | 7 | 8 | 9 | 10 |
|---|---|---|---|---|---|---|---|---|---|---|
| Real-time degree | 0.018 | 0.036 | 0.054 | 0.072 | 0.09 | 0.109 | 0.127 | 0.145 | 0.163 | 0.181 |
| Real-time weight (variation factor = 2) | 1 | 4 | 9 | 16 | 25 | 36 | 49 | 64 | 81 | 100 |
| Real-time degree | 0.002 | 0.01 | 0.023 | 0.041 | 0.064 | 0.093 | 0.127 | 0.166 | 0.21 | 0.259 |

Figure 2:
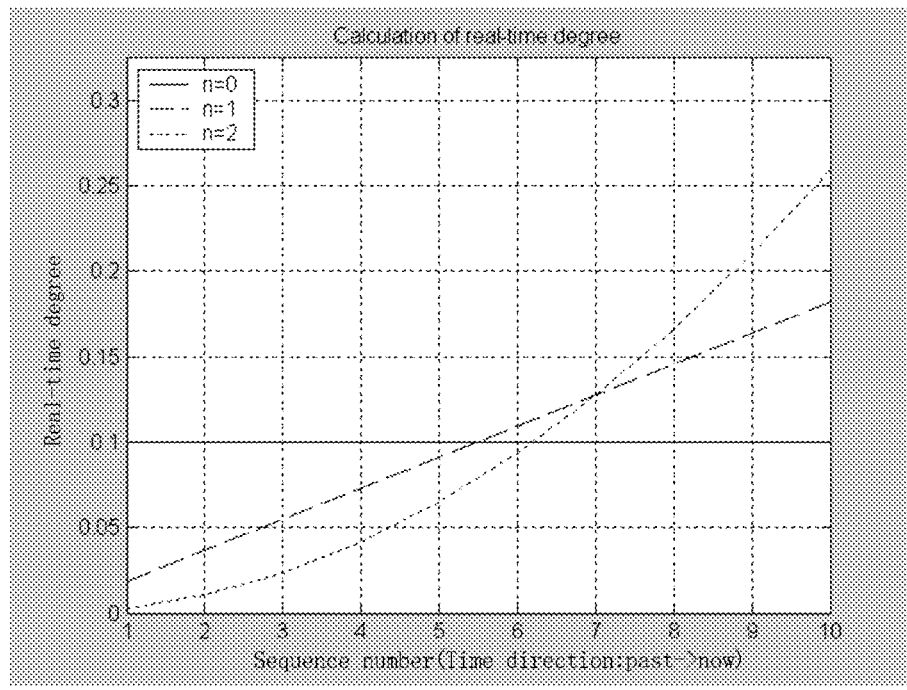
FIG. 2 shows a simulated diagram of relationship between real-time degree and respiratory cycle according to the method for detecting respiratory rate shown in FIG. 1.

The above table may be best depicted with a view in MATLAB, for example, as shown in FIG. 2, where n is the variation factor.

It may be seen from the real-time degree calculation formula that the real-time degree of a certain respiratory cycle is related to the variation factor n and the sequence number. From the determination of the variation factor n and the sequence number of the respiratory cycle, it may be known that a sequence number indicating the position for a preceding respiratory cycle is smaller than a sequence number indicating the position for a subsequent respiratory cycle, and a higher variation degree corresponds to a smaller variation factor n so that a mapping relationship occurs between the real-time degree and the variation degree. This relationship may be indicated with the variation factor. For respiratory cycles with a higher variation degree, a smaller variation factor is selected and the difference between real-time degrees of respiratory cycles at different time sequence is smaller s, so that the calculated stability of the respiratory rate might increase. For respiratory cycles with a smaller variation degree, a larger variation factor is selected and the difference between real-time degrees of respiratory cycles at different time sequence is large (the real-time degree of a respiratory cycle which is closer to the current moment is higher), so that the instantaneity of the calculated respiratory rate could be increased. Thereby realizing increasing stability for respiratory cycles with larger variation and increasing real-time degree for respiratory cycles with smaller variation degree.

At step 7, respiratory rate is calculated.

Figure 6:
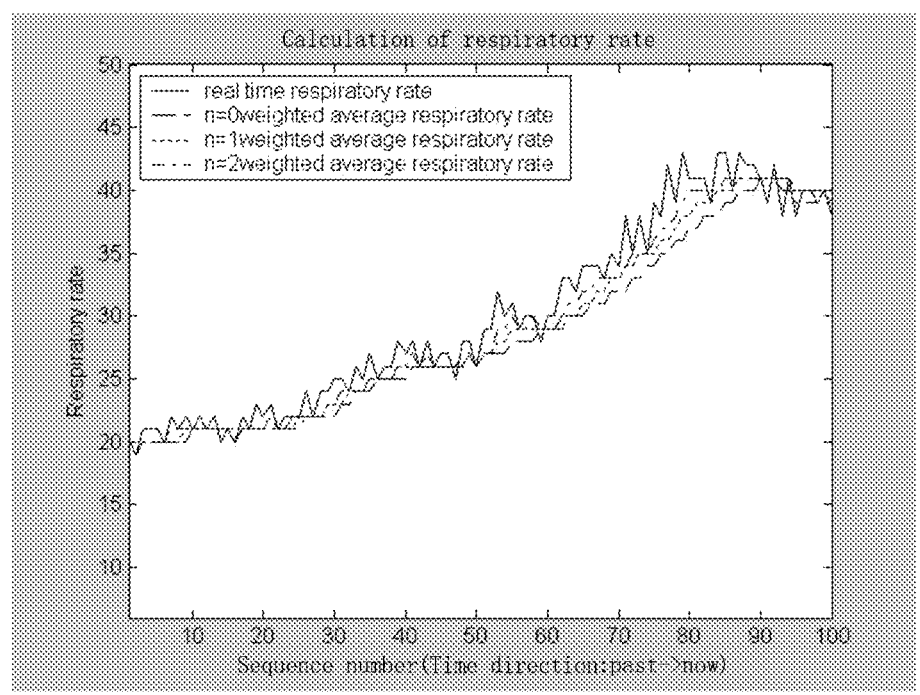
FIG. 6 shows a simulated diagram of relationship between respiratory rate and respiratory cycle according to the method for detecting respiratory rate shown in FIG. 1.

The respiratory rate may be calculated by:

$$rtav = \sum_{i=1}^{sl} rr(i) * rt(i);$$

where rtav represents the respiratory rate, i is the sequence number of the respiratory cycle, rt(i) is the real-time degree of the i-th respiratory cycle, and rr(i) is the respiratory rate of the i-th respiratory cycle. The calculation of the smoothed respiratory rate may be best depicted with a view in MATLAB, for example, as shown in FIG. 6, where n is the weighting factor.

Figure 7:
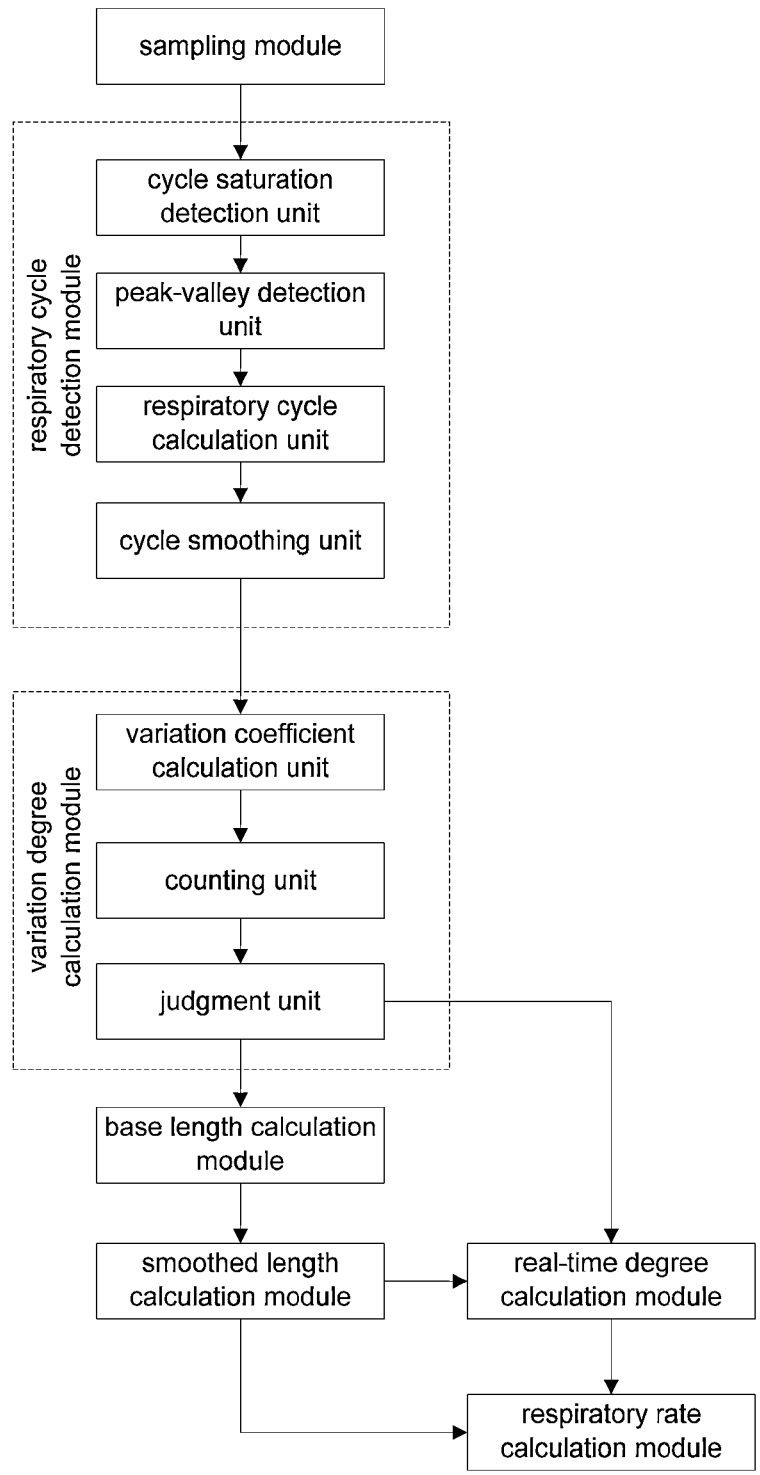
FIG. 7 shows a schematic diagram of an apparatus for detecting respiratory rate according to an embodiment.

As shown in FIG. 7, in one embodiment, an apparatus for detecting respiratory rate may include a sampling module, a respiratory cycle detection module, a variation degree calculation module, a base length calculation module, a smoothed length calculation module, a real-time degree calculation module and a respiratory rate calculation module.

The sampling module samples received respiratory waveform data within a time period in a time sequence to obtain a group of samples.

The respiratory cycle detection module detects respiratory cycles from the group of samples, which may include a cycle saturation detection unit for judging whether each respiratory cycle is saturated respectively; a peak-valley detection unit for detecting peaks and valleys from the group of samples; and a respiratory cycle calculation unit for calculating duration of the respiratory cycle on the time difference between two adjacent peaks or valleys.

In addition, the respiratory cycle detection module may further include a cycle smoothing unit for smoothing the current respiratory cycle by the duration of the previous respiratory cycle if duration difference between the current and previous respiratory cycles is equal to or great than a difference threshold and the current respiratory cycle is saturated.

The variation degree calculation module calculates the variation degree, which may include a variation coefficient calculation unit, a counting unit and a judgment unit. The variation degree calculation unit calculates a set of variation coefficients for the group of samples, and the specific calculation method is the same as above method. The counting unit counts numbers lcnt and mcnt of variation coefficient belonged to [0, lcv] and [0, mcv] respectively, where lcv is a smaller critical value, mcv is an intermediate critical value and 0≤lcv<mcv<2. The judgment unit judges whether $$\frac{lcnt}{N}$$

is greater than or equal to a first threshold (such as whether $$\frac{lcnt}{N} \geq 80\%\bigg);$$

If yes, the variation degree for the group of samples is considered low; or further judges whether $$\frac{mcnt}{N}$$

is greater than or equal to the first threshold (such as whether $$\frac{mcnt}{N} \geq 80\%),$$

if yes, the variation degree for the group of samples is considered intermediate, or the variation degree for the group of samples is considered high.

In the embodiment, a variation factor could be used to represent the variation degree. When the variation degree for the group of samples is high, the variation factor n is 0; when the variation degree for the group of samples is intermediate, the variation factor n is 1; when the variation degree for the group of samples is low, the variation factor is 2.

The value of the base length is adopted as the bigger one from a reference cycles number and a minimum empirical period number during a predetermined time, and the number of respiratory cycles calculated base on the previous respiratory rate and the predetermined time period. The specific calculation method is the same as above method.

The smoothed length calculation module calculates smoothed length by calculated base length. Specifically, the smoothed length calculation module calculates the smoothed length is calculated by:

$$\sum_{i=sl-bl+1}^{sl} i^n \geq th_2 * \sum_{i=1}^{sl} i^n;$$

where i is the sequence number indicating the position of the respiratory cycle, n is the variation factor, th2 is a second threshold, bl is the base length, sl is the smoothed length, and sl is the minimum integer satisfying the equation.

The real-time degree calculation module calculates real-time degree of each respiratory cycle base on the variation degree, sequence number of each respiratory cycle and the smoothed length. Specifically, the real-time degree calculation module calculates the real-time degree of each respiratory cycle by:

$$rt(i) = \frac{i^n}{\sum_{i=1}^{sl} i^n};$$

where i is the sequence number of the corresponding respiratory cycle, n is the variation factor, sl is the smoothed length and rt is the real-time degree.

The respiratory rate calculation module calculates smoothed respiratory rate base on the smoothed length and the real-time degree. Specifically, the smoothed length calculation module calculates the smoothed length is calculated by:

$$\sum_{i=sl-bl+1}^{sl} i^n \geq th_2 * \sum_{i=1}^{sl} i^n;$$

where i is the sequence number indicating the position of the respiratory cycle, n is the variation factor, th2 is a second threshold, bl is the base length, sl is the smoothed length, and sl is the least integer satisfying the equation.

In conclusion, for respiration with larger variations, using smaller variation degree and larger base length, stability of the respiratory rate could be enhanced and timeless change could be reflected; for respiration with smaller variations, using higher variation degree and less base length, the timeless change could be enhanced and respiratory rate change could be reflected in shorter time; for respiration with larger respiratory rate, use more respiratory cycles to do smoothing process, so as to enhance stability; for respiration with lower respiratory rate, use less respiratory cycles to do smoothing process, so as to reflect timeless change. In practical application, the stability and timeless change of the respiratory rate could be obtained better overall results by the variation factor and the base length.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, advantages, and solutions to problems have been described above with regard to various embodiments and are not to be construed as critical, required, or essential feature or element. The scope of the present disclosure should, therefore, be determined by the following claims.

What is claimed is:

1. A method of determining a respiratory rate, the method comprising:
    A0. measuring, with a pneumograph, respiratory waveform data;
    A1. sampling the respiratory waveform data with a physiological parameters monitor;
    B1. detecting respiratory cycles comprising segments of sampled respiratory waveform data corresponding to amounts of time between at least one of adjacent peaks and adjacent valleys of the sampled respiratory waveform data;
    C1. calculating a variation degree indicating a degree of variation between sample points for groups of sample points of the sampled respiratory waveform data;
    D1. determining a base length computed as a function of at least the variation degree, wherein the higher the variation degree is, the faster the base length increases with an increase in a respiratory rate corresponding to the respiratory waveform data;
    E1. calculating a smoothed length based, at least in part, on the base length;
    F1. calculating a real-time degree for each of the detected respiratory cycles based, at least in part, on the variation degree, a sequence number of each of the detected respiratory cycles, and the smoothed length; and
    G1. calculating respiratory rate based, at least in part, on the smoothed length and the calculated real-time degrees.

2. The method of claim 1, further comprising, B13. calculating durations of the respiratory cycles by determining a difference in time between the at least one of the adjacent peaks and the adjacent valleys for each of the determined respiratory cycles.

3. The method of claim 2, further comprising determining that a current duration of a current respiratory cycle is equal to a previous duration of a previous respiratory cycle if a difference between a calculated duration of the current respiratory cycle and the previous duration of the previous respiratory cycle surpasses a predetermined difference threshold.

4. The method of claim 1, wherein C1. calculating a variation degree indicating a degree of variation between sample points for groups of sample points comprises:
    C11. calculating a set of variation coefficients for the sampled respiratory waveform data;
    C12. determining a number lcnt of variation coefficients of the calculated set of variation coefficients falling within a first range from 0 to lcv, and a number mcnt of variation coefficients of the calculated set of variation coefficients falling within a second range 0 to mcv, wherein lcv is a relatively small critical value, and mcv is an intermediate critical value, and $0 \leq lcv < mcv < 2$; and C13. determining that the variation degree is low if $$\frac{lcnt}{N}$$

is greater than or equal to a first predetermined threshold, determining that the variation degree is intermediate if $$\frac{mcnt}{N}$$

is greater than the first predetermined threshold, and determining that the variation degree is high otherwise, wherein N is a number of samples of the sampled respiratory waveform data.

5. The method of claim 4, wherein the first predetermined threshold is about 80%.

6. The method of claim 4, wherein the base length is determined to be a larger one of a reference cycles number and a minimum empirical period number during a predetermined time;
  wherein:
    the predetermined time is a first time period if the variation degree is determined to be low,
    the predetermined time is a second time period if the variation degree is determined to be intermediate,
    the predetermined time is a third time period if the variation degree is determined to be high,
    the first time period is less than the second time period, which is less than the third time period,
    the reference cycles number is a number of respiratory cycles calculated based, at least in part, on a previous respiratory rate, and
    the minimum empirical period number is an empirically determined minimum value for the base length at the predetermined time.

7. The method of claim 6, wherein the number of respiratory cycles is also calculated based, at least in part, on the predetermined time period.

8. The method of claim 4, wherein the smoothed length is calculated by:

$$\sum_{i=sl-bl+1}^{sl} l^n \geq th_2 * \sum_{i=1}^{sl} l^n;$$

wherein i is the sequence number indicating the position of the respiratory cycle, n is a variation factor corresponding to the calculated variation degree, th2 is a second threshold, bl is the base length, sl is the smoothed length, and sl is the minimum integer satisfying the equation;
wherein if the variation degree is determined to be high, the variation factor n is 0; if the variation degree is determined to be intermediate, the variation factor n is 1; and if the variation degree is determined to be low, the variation factor is 2.

9. The method of claim 4, wherein said real-time degree of each respiratory cycle is calculated by:

$$rt(i) = \frac{l^n}{\sum_{i=1}^{sl} l^n};$$

wherein i is the sequence number of the corresponding respiratory cycle, n is the variation factor, sl is the smoothed length and rt is the real-time degree;
wherein if the variation degree is determined to be high, the variation factor n is 0; if the variation degree is determined to be intermediate, the variation factor n is 1; and if the variation degree is determined to be low, the variation factor is 2.

10. The method of claim 1, wherein the respiratory rate is calculated by:

$$rtav = \sum_{i=1}^{sl} rr(i) * rt(i);;$$

wherein rtav is the respiratory rate, i is the sequence number of the respiratory cycle, rt(i) is the real-time degree of the i-th respiratory cycle, and rr(i) is the respiratory rate of the i-th respiratory cycle.

11. An apparatus, for detecting respiratory rate, comprising:
  a pneumograph configured to generate respiratory waveform data; and
  a physiological parameters monitor configured to receive the respiratory waveform data from the pneumograph, the physiological parameters monitor comprising:
    a sampling module configured to sample received respiratory waveform data in a time sequence;
    a respiratory cycle detection module configured to detect respiratory cycles from the sampled respiratory waveform data;
    a variation degree calculation module configured to calculate a variation degree for the sampled respiratory waveform data;
    a base length calculation module configured to calculate a base length based, at least in part, on the calculated variation degree;
    a smoothed length calculation module configured to calculate a smoothed length based, at least in part, on the calculated base length;
    a real-time degree calculation module configured to calculate a real-time degree of each respiratory cycle based, at least in part, on the variation degree, a sequence number of each respiratory cycle, and the smoothed length; and
    a respiratory rate calculation module configured to calculate a respiratory rate base on the smoothed length and the real-time degree.

12. The apparatus of claim 11, wherein the respiratory cycle detection module comprises:
  a peak-valley detection unit configured to detect peaks and valleys from the sampled respiratory waveform data; and
  a respiratory cycle calculation unit configured to detect a duration of the respiratory cycle based, at least in part, on a time difference between one of two adjacent peaks and two adjacent valleys in the sampled respiratory waveform data.

13. The apparatus of claim 12, wherein the respiratory cycle detection module further comprises a cycle smoothing unit configured to determine that a current duration of a current respiratory cycle is equal to a previous duration of a previous respiratory cycle if a difference between a calculated duration of the current respiratory cycle and the previous duration of the previous respiratory cycle surpasses a predetermined difference threshold.

14. The apparatus of claim 11, wherein the variation degree calculation module comprises:
   a variation coefficient calculation unit configured to calculate a set of variation coefficients for the sampled respiratory waveform data;
   a counting unit configured to determine a number lcnt of variation coefficients of the calculated set of variation coefficients falling within a first range from 0 to lcv, and a number mcnt of variation coefficients of the calculated set of variation coefficients falling within a second range 0 to mcv, relatively small critical value, mcv is an intermediate critical value, and 0≤lcv<mcv<2; and
   a judgment unit configured to determine that:
      the variation degree is low if $$\frac{lcnt}{N}$$

is greater man or equal to a first threshold;
      the variation degree is intermediate if $$\frac{mcnt}{N}$$

is greater than or equal to the first threshold;
      the variation degree is high otherwise;
   wherein N is a number of samples of the sampled respiratory waveform data.

15. The apparatus of claim 14, wherein the base length is calculated to be a larger one of a reference cycles number and a minimum empirical period number during a predetermined time;
   wherein:
      the predetermined time is a first time period if the variation degree is determined to be low,
      the predetermined time is a second time period if the variation degree is determined to be intermediate,
      the predetermined time is a third time period if the variation degree is determined to be high,
      the first time period is less than the second time period, which is less than the third time period;
      the reference cycles number is a number of respiratory cycles calculated based, at least in part, on a previous respiratory rate, and
      the minimum empirical period number is an empirically determined minimum value for the base length at the predetermined time.

16. The apparatus of claim 15, wherein the number of respiratory cycles is also calculated based, at least in part, on the predetermined time period.

17. The apparatus claim 14, wherein the smoothed length calculation module calculates the smoothed length according to:

$$\sum_{i=sl-bl+1}^{sl} i^n \geq th_2 * \sum_{i=1}^{sl} i^n;$$

wherein i is the sequence number indicating the position of the respiratory cycle, n is a variation factor corresponding to the calculated variation degree, th2 is a second threshold, bl is the base length, sl is the smoothed length, and sl is the minimum integer satisfying the equation;
   wherein if the variation degree is determined to be high, the variation factor n is 0; if the variation degree is determined to be intermediate, the variation factor n is 1; and if the variation degree is determined to be low, the variation factor is 2.

18. The apparatus of claim 14, wherein the real-time degree calculation module calculates the real-time degree of each respiratory cycle according to:

$$rt(i) = \frac{i^n}{\sum_{i=1}^{sl} i^n};$$

wherein i is the sequence number of the corresponding respiratory cycle, n is the variation factor, sl is the smoothed length and rt is the real-time degree;
   wherein if the variation degree is determined to be high, the variation factor n is 0; if the variation degree is determined to be intermediate, the variation factor n is 1; if the variation degree is determined to be low, the variation factor is 2.

19. The apparatus of claim 11, wherein the respiratory rate calculation module calculates the smoothed respiratory according to:

$$rtav = \sum_{i=1}^{sl} rr(i) * rt(i);$$

wherein rtav is the respiratory rate, i is the sequence number of the respiratory cycle, rt(i) is the real-time degree of the i-th respiratory cycle, and rr(i) is the respiratory rate of the i-th respiratory cycle.

* * * * *